US008805497B2

(12) United States Patent
Dong et al.

(10) Patent No.: US 8,805,497 B2
(45) Date of Patent: Aug. 12, 2014

(54) TITRATED INTERMITTENT PACING THERAPY (75) Inventors: Yanting Dong, Shoreview, MN (US); Shantha Arcot-Krishnamurthy, Vadnais Heights, MN (US); Allan C. Shuros, St. Paul, MN (US); David L. Whitehouse, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 761 days.

(21) Appl. No.: 12/573,533

(22) Filed: Oct. 5, 2009

(65) Prior Publication Data

US 2010/0087887 A1  Apr. 8, 2010

Related U.S. Application Data (60) Provisional application No. 61/103,033, filed on Oct. 6, 2008.

(51) Int. Cl.
*A61N 1/365* (2006.01)

(52) U.S. Cl.
USPC .......... 607/9; 607/5; 607/11; 607/17; 607/25; 600/16

(58) Field of Classification Search
USPC .................. 600/16; 607/5, 9, 11, 17, 25
See application file for complete search history.

(56) References Cited

U.S. PATENT DOCUMENTS

| 5,601,613 | A | * | 2/1997 | Florio et al. | 607/14 |
|---|---|---|---|---|---|
| 5,968,081 | A | * | 10/1999 | Levine | 607/9 |
| 7,295,874 | B2 | | 11/2007 | Prinzen et al. | |
| 7,308,306 | B1 | * | 12/2007 | Park et al. | 607/9 |
| 7,450,988 | B2 | | 11/2008 | Ross et al. | |
| 7,587,238 | B2 | * | 9/2009 | Moffitt et al. | 607/9 |
| 7,711,420 | B2 | | 5/2010 | Baynham et al. | |
| 7,778,707 | B2 | * | 8/2010 | Shuros et al. | 607/11 |
| 8,195,290 | B2 | * | 6/2012 | Brockway et al. | 607/3 |
| 8,401,642 | B2 | * | 3/2013 | Shipley et al. | 607/17 |
| 2005/0065568 | A1 | | 3/2005 | Liu et al. | |
| 2005/0096705 | A1 | * | 5/2005 | Pastore et al. | 607/17 |
| 2005/0177195 | A1 | * | 8/2005 | Salo | 607/11 |

(Continued)

FOREIGN PATENT DOCUMENTS

| WO | WO-93/02745 A1 | 2/1993 |
|---|---|---|
| WO | WO-2004/024229 A1 | 3/2004 |
| WO | WO-2006/105474 A2 | 10/2006 |
| WO | WO-2010/042535 A2 | 4/2010 |

OTHER PUBLICATIONS

"International Application Serial No. PCT/US2009/059718, International Search Report mailed Jul. 1, 2010", 5 pgs.

(Continued)

*Primary Examiner* — Niketa Patel
*Assistant Examiner* — Christopher A Flory
(74) *Attorney, Agent, or Firm* — Schwegman Lundberg & Woessner, P.A.

(57) ABSTRACT

Cardioprotective pre-excitation pacing may be applied to stress or de-stress a particular myocardial region delivering of pacing pulses in a manner that causes a dyssynchronous contraction. Such dyssynchronous contractions are responsible for the desired cardioprotective effects of pre-excitation pacing but may also be hazardous. Described herein is a method and system that uses measures of a patient's heart rate or exertion level to control the duty cycles of intermittent pre-excitation pacing.

20 Claims, 4 Drawing Sheets

(56) References Cited

U.S. PATENT DOCUMENTS

| | | | |
|---|---|---|---|
| 2005/0267542 A1* | 12/2005 | David et al. | 607/17 |
| 2005/0288720 A1* | 12/2005 | Ross et al. | 607/9 |
| 2006/0241704 A1 | 10/2006 | Shuros et al. | |
| 2006/0247702 A1 | 11/2006 | Stegemann et al. | |
| 2006/0253156 A1 | 11/2006 | Pastore et al. | |
| 2006/0259087 A1 | 11/2006 | Baynham et al. | |
| 2006/0259088 A1 | 11/2006 | Pastore et al. | |
| 2006/0287684 A1 | 12/2006 | Baynham et al. | |
| 2007/0016259 A1 | 1/2007 | Bakken et al. | |
| 2007/0150005 A1 | 6/2007 | Sih et al. | |
| 2007/0191892 A1 | 8/2007 | Mullen et al. | |
| 2008/0004669 A1 | 1/2008 | Sathaye et al. | |
| 2008/0119904 A1 | 5/2008 | Salo et al. | |
| 2008/0161894 A1* | 7/2008 | Ben-David et al. | 607/116 |
| 2008/0234772 A1* | 9/2008 | Shuros et al. | 607/11 |
| 2008/0234774 A1 | 9/2008 | Baynham et al. | |
| 2009/0082823 A1* | 3/2009 | Shuros et al. | 607/17 |
| 2009/0171407 A1* | 7/2009 | Salo | 607/3 |
| 2009/0306734 A1* | 12/2009 | Moffitt et al. | 607/19 |

OTHER PUBLICATIONS

"International Application Serial No. PCT/US2009/059718 Written Opinion mailed Jul. 1, 2010", 7 pgs.

"U.S. Appl. No. 11/687,957, Notice of Allowance mailed Dec. 21, 2009", 8 pgs.

"U.S. Appl. No. 11/687,957, Non-Final Office Action mailed Mar. 6, 2009", 7 pgs.

"U.S. Appl. No. 11/687,957, Response filed Aug. 6, 2009 to Non-Final Office Action mailed Mar. 6, 2009", 17 pgs.

"International Application Serial No. PCT/US2008/003594, International Search Report mailed Jul. 9, 2008", 5 pgs.

"International Application Serial No. PCT/US2008/003594, Written Opinion mailed Jul. 9, 2008", 6 pgs.

"International Application Serial No. PCT/US2009/059718, Invitation to Pay Additional Fees and Partial Search Report mailed Apr. 7, 2010", 7 pgs.

Ovize, M., et al., "Stretch preconditions canine myocardium.", *Am J Physiol.*, 266(1 Pt 2), (Jan. 1994), H137-H146.

Prinzen, F. W., et al., "Relation between the pacing induced sequence of activation and left ventricular pump function in animals.", *Pacing Clin Electrophysiol.*, 25(4 Pt 1), (Apr. 2002), 484-98.

Prinzen, Frits W, "Mapping of regional myocardial strain and work during ventricular pacing: experimental study using magnetic resonance imaging tagging", *Journal of the American College of Cardiology*, 33(6), (May 1999), 1735-1742

Vanagt, W. Y., et al., "Pacing-induced dys-synchrony preconditions rabbit myocardium against ischemia/reperfusion injury.", *Circulation*, 114(1 Suppl), (Jul. 4, 2006), 1264-1269.

"Japanese Application Serial No. 2011-531118, Office Action Mailed Nov. 24, 2012", With English Translation, 6 pgs.

\* cited by examiner

TITRATED INTERMITTENT PACING THERAPY

CROSS REFERENCE TO RELATED APPLICATIONS

This application claims the benefit of U.S. Provisional Application No. 61/103,033, filed on Oct. 6, 2008, under 35 U.S.C. §119(e), which is hereby incorporated by reference.

This application is related to U.S. patent application Ser. No. 11/687,957 filed on Mar. 19, 2007 and assigned to Cardiac Pacemakers, Inc., the disclosure of which is incorporated by reference in its entirety.

FIELD OF THE INVENTION

This invention pertains to cardiac rhythm management devices such as pacemakers and other implantable devices.

BACKGROUND

Heart failure (HF) is a debilitating disease that refers to a clinical syndrome in which an abnormality of cardiac function causes a below normal cardiac output that can fall below a level adequate to meet the metabolic demand of peripheral tissues. Heart failure can be due to a variety of etiologies with ischemic heart disease being the most common. Inadequate pumping of blood into the arterial system by the heart is sometimes referred to as "forward failure," with "backward failure" referring to the resulting elevated pressures in the lungs and systemic veins which lead to congestion. Backward failure is the natural consequence of forward failure as blood in the pulmonary and venous systems fails to be pumped out. Forward failure can be caused by impaired contractility of the ventricles due, for example, to coronary artery disease, or by an increased afterload (i.e., the forces resisting ejection of blood) due to, for example, systemic hypertension or valvular dysfunction. One physiological compensatory mechanism that acts to increase cardiac output is due to backward failure which increases the diastolic filling pressure of the ventricles and thereby increases the preload (i.e., the degree to which the ventricles are stretched by the volume of blood in the ventricles at the end of diastole). An increase in preload causes an increase in stroke volume during systole, a phenomena known as the Frank-Starling principle. Thus, heart failure can be at least partially compensated by this mechanism but at the expense of possible pulmonary and/or systemic congestion.

When the ventricles are stretched due to the increased preload over a period of time, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium which leads to alterations in cellular structure, a process referred to as ventricular remodeling. Ventricular remodeling leads to further dysfunction by decreasing the compliance of the ventricles (thereby increasing diastolic filling pressure to result in even more congestion) and causing eventual wall thinning that causes further deterioration in cardiac function. It has been shown that the extent of ventricular remodeling is positively correlated with increased mortality in HF patients.

Remodeling is thought to be the result of a complex interplay of hemodynamic, neural, and hormonal factors that occur primarily in response to myocardial wall stress. As noted above, one physiological compensatory mechanism that acts to increase cardiac output is increased diastolic filling pressure of the ventricles as an increased volume of blood is left in the lungs and venous system, thus increasing preload. The ventricular dilation resulting from the increased preload causes increased ventricular wall stress at a given systolic pressure in accordance with Laplace's law. Along with the increased pressure-volume work done by the ventricle, this acts as a stimulus for compensatory hypertrophy of the ventricular myocardium. Hypertrophy can increase systolic pressures but, if the hypertrophy is not sufficient to meet the increased wall stress, further and progressive dilation results. This non-compensatory dilation causes wall thinning and further impairment in left ventricular function. It also has been shown that the sustained stresses causing hypertrophy may induce apoptosis (i.e., programmed cell death) of cardiac muscle cells. Although ventricular dilation and hypertrophy at first may be compensatory and increase cardiac output, the process ultimately results in further deterioration and dysfunction.

DETAILED DESCRIPTION

Described herein is a method and device for delivering electrical stimulation to the heart in a manner that advantageously redistributes myocardial stress during systole for therapeutic purposes in the treatment of, for example, patients with ischemic heart disease, post-MI patients, and HF patients. Myocardial regions that contract earlier during systole experience less wall stress than later contracting regions. Pacing pulses may be delivered to a particular myocardial region to pre-excite that region relative to other regions during systole, with the latter being excited by intrinsic activation or a subsequent pacing pulse. (As the term is used herein, a pacing pulse is any type of electrical stimulation that excites the myocardium, whether or not used to enforce a particular rate.) As compared with an intrinsic contraction, the pre-excited region is mechanically unloaded or de-stressed, while the later excited regions are subjected to increased stress. Such pre-excitation pacing may be applied to deliberately de-stress a particular myocardial region that may be expected to undergo deleterious remodeling, such as the area around a myocardial infarct or a hypertrophying region. Pre-excitation pacing may also be applied to deliberately stress a region remote from the pre-excitation pacing site in order to exert a conditioning effect, similar to the beneficial effects of exercise. Whether for intentionally stressing or de-stressing a myocardial region, such cardioprotective pre-excitation pacing may be applied intermittently, either according to a defined schedule or upon detection of specified entry or exit conditions, and is referred to herein as intermittent pacing therapy or IPT.

As explained above, pacing pulses may be used to pre-excite a region of the heart so that it contracts before later-excited regions and experiences less stress during systole. This is in contradistinction to the normal physiological situation where, due the heart's specialized conduction system, the spread of depolarization throughout the myocardium is very rapid and results in a synchronous contraction. If the contractility of the myocardial tissue is normal, a synchronous contraction is hemodynamically more effective in pumping blood. Cardiac resynchronization pacing attempts to restore synchronous contractions in patients having ventricular conduction abnormalities by delivering pacing pulses to the heart in a manner that results in a more synchronous contraction than would otherwise occur. Pre-excitation pacing applied to stress or de-stress a particular myocardial region for a cardioprotective effect, on the other hand, is the delivery of pacing pulses in a manner that causes a dyssynchronous contraction. Such dyssynchronous contractions are responsible for the desired cardioprotective effects of pre-excitation pacing but may also be hazardous. Described herein is a method and device that uses measures of a patient's heart rate or exertion level to control the delivery of IPT.

Mechanical Effects of Pacing Therapy

When the ventricles are stimulated to contract by a pacing pulse applied through an electrode located at a particular pacing site, the excitation spreads from the pacing site by conduction through the myocardium. This is different from the normal physiological situation, where the spread of excitation to the ventricles from the AV node makes use of the heart's specialized conduction system made up of Purkinje fibers which allows a rapid and synchronous excitation of the entire ventricular myocardium. The excitation resulting from a pacing pulse, on the other hand, produces a relatively asynchronous contraction due to the slower velocity at which excitation is conducted from the pacing site to the rest of the myocardium. Regions of the myocardium located more distally from the pacing site are thus excited later than regions proximal to the pacing site as compared with an intrinsic contraction. As explained below, this results in a re-distribution of myocardial wall stress.

The degree of tension on a muscle fiber before it contracts is termed the preload, while the degree of tension on a muscle fiber as it contracts is termed the afterload. Increasing the preload stretches a muscle fiber and also increases its maximum tension and velocity of shortening during contraction. With respect to the heart, the preload of a particular myocardial region is the myocardial wall stress at the end of diastole due to end-diastolic pressure and the forces applied by adjacent regions. The afterload of a myocardial region is the myocardial wall stress during systole due to the pressure load that the heart must pump against. When a myocardial region contracts late relative to other regions, the contraction of those other regions stretches the later contracting region and increases its preloading, thus causing an increase in the contractile force generated by the region. Conversely, a myocardial region that contracts earlier relative to other regions experiences decreased preloading and generates less contractile force. Because pressure within the ventricles rises rapidly from a diastolic to a systolic value as blood is pumped out into the aorta and pulmonary arteries, the parts of the ventricles that contract earlier during systole do so against a lower afterload than do parts of the ventricles contracting later. Delivery of a pacing pulse to a ventricular region makes that region contract earlier than other parts of the ventricle. The paced region will therefore be subjected to both a decreased preload and afterload which decreases the mechanical stress experienced by the region relative to other regions during systolic contraction. A region remote from the paced region, on the other hand, will experience increased mechanical stress as it contracts later during systole due to either conduction from the pre-excited site, a subsequent pace applied to the remote region, or intrinsic activation conducted from the AV node.

Applications of Stress Reducing Pre-Excitation Pacing

All but a small fraction of the total amount of oxygen consumed by the myocardium is for the purpose of active muscular contraction during systole, and the oxygen demand of a particular myocardial region increases with increasing systolic wall stress. Causing a particular myocardial region to contract earlier relative to other regions will thus lessen its metabolic demands and the degree of any ischemia that may be present. Particular myocardial regions may also be vulnerable to undergoing deleterious remodeling as a result of increased wall stress in post-MI or HF patients. In order to cause early contraction and lessened stress to a myocardial region vulnerable to becoming ischemic or undergoing remodeling, pre-excitation pacing pulses may be delivered to one or more sites in or around the vulnerable region in a manner that pre-excites those sites relative to the rest of the ventricle and mechanically unloads the vulnerable region. Pre-excitation pacing therapy to unload a vulnerable region may be implemented by pacing the ventricles at a single site in proximity to the vulnerable region or by pacing at multiple ventricular sites in such proximity. In the latter case, the pacing pulses may be delivered to the multiple sites simultaneously or in a defined pulse output sequence. The single-site or multiple site pacing may be performed in accordance with a bradycardia pacing algorithm such as an inhibited demand mode or a triggered mode.

Applications of Stress Augmenting Pre-Excitation Pacing

Another use of pre-excitation pacing is to intentionally stress a region vulnerable to ischemia by pacing at a site(s) remote from the vulnerable region. As described above, such pacing causes increased mechanical stress to the vulnerable region by delaying its contraction during systole relative to other regions. Intermittently stressing a vulnerable region may cause a low level of myocardial ischemia in the region in a patient with demand ischemia, thereby promoting angiogenesis and pre-conditioning the vulnerable region to better withstand the effects of a subsequent ischemic episode. Stress augmentation pacing may also be applied to a weakened region or to a large part of the myocardium in the form of an asynchronous contraction in order to exert a pre-conditioning effect similar to exercise. Pre-excitation pacing therapy to augment stress may be implemented by pacing the ventricles at a single site or multiple sites remote from the region(s) desired to be stressed in accordance with a bradycardia pacing algorithm such as an inhibited demand mode or a triggered mode. Multiple pacing pulses may be delivered to the multiple sites simultaneously or in a defined pulse output sequence.

Exemplary Implantable Device

Figure 1:
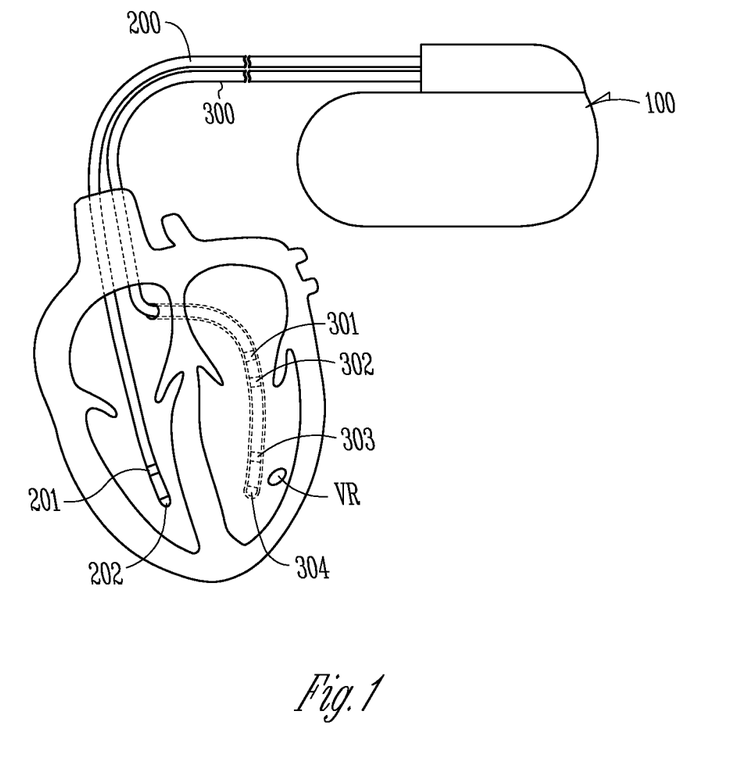
FIG. 1 illustrates the physical configuration of an exemplary pacing device.

FIG. 1 shows an exemplary implantable cardiac device 100 for delivering pre-excitation pacing for the purpose of stressing or de-stressing one or more myocardial regions. In addition, the device may have the capability of delivering other types of pacing therapy such as bradycardia pacing and cardiac resynchronization pacing. As will be described below, the device may be configured to switch between a normal operating mode and a pre-excitation mode for delivering pre-excitation pacing in accordance with defined entry and exit conditions. Implantable pacing devices are typically placed subcutaneously or submuscularly in a patient's chest with leads threaded intravenously into the heart to connect the device to electrodes disposed within a heart chamber that are used for sensing and/or pacing of the chamber. Electrodes may also be positioned on the epicardium by various means. A programmable electronic controller causes the pacing pulses to be output in response to lapsed time intervals and/or sensed electrical activity (i.e., intrinsic heart beats not as a result of a pacing pulse). The device senses intrinsic cardiac electrical activity through one or more sensing channels, each of which is connected to one or more of the electrodes. In order to excite myocardial tissue in the absence of an intrinsic beat, pacing pulses with energy above a certain threshold are delivered to one or more pacing sites through one or more pacing channels, each of which incorporates one or more of the electrodes. FIG. 1 shows the exemplary device having two leads 200 and 300, each of which is a multi-polar (i.e., multi-electrode) lead having electrodes 201-202 and 301-304, respectively. The electrodes 201-202 are disposed in the right ventricle in order to excite or sense right ventricular and/or septal regions, while the electrodes 301-304 are disposed in the coronary sinus or left cardiac veins in order to excite or sense regions of the left ventricle. If a region VR that is vulnerable to remodeling or ischemia were located in the apical region of the left ventricle, pre-excitation pacing to the region could be delivered via electrodes 303 and 304 in a bipolar pacing configuration to de-stress and unload the vulnerable region. Such pre-excitation pacing could be delivered, for example, as left ventricular-only pacing or as biventricular pacing with an offset such that the left ventricle is paced before the right. Conversely, if it were desired to deliberately stress the region VR for cardioprotective pre-conditioning, pre-excitation pacing could be delivered via electrodes 201 and 202 in a right ventricle-only pacing mode or electrodes 301 and 302 in a left ventricle-only or biventricular pacing mode in order to pre-excite a myocardial region remote from the region VR. Other embodiments may use any number of electrodes in the form of unipolar and/or multi-polar leads in order to excite different myocardial sites. As explained below, once the device and leads are implanted, the pacing and/or sensing channels of the device may be configured with selected ones of the multiple electrodes in order to selectively pace or sense a particular myocardial site(s).

Figure 2:
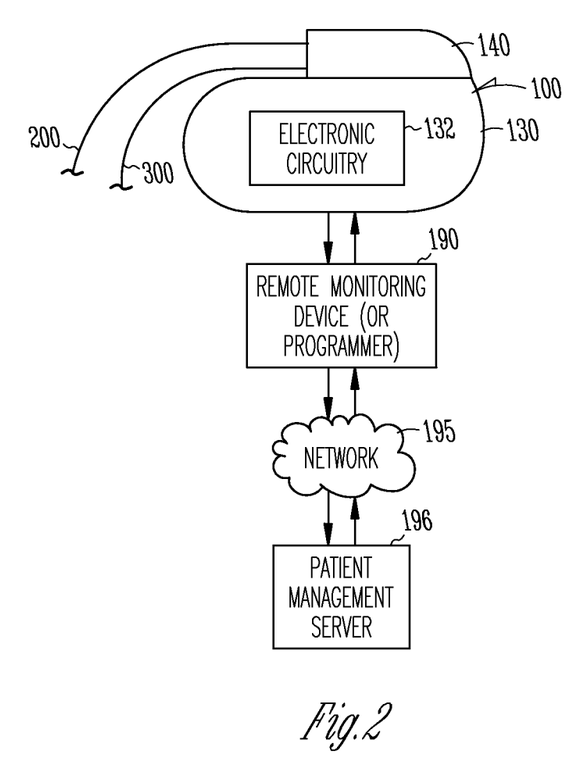
FIG. 2 shows the components of an exemplary device.

FIG. 2 shows the components of the implantable device 100 in more detail as well as an exemplary monitoring/programming system. The implantable device 100 includes a hermetically sealed housing 130 that is placed subcutaneously or submuscularly in a patient's chest. The housing 130 may be formed from a conductive metal, such as titanium, and may serve as an electrode for delivering electrical stimulation or sensing in a unipolar configuration. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device 190. An external programmer wirelessly communicates with the device 100 and enables a clinician to receive data and modify the programming of the controller. A remote monitoring device also communicates via telemetry with the device 100 and may be further interfaced to a network 195 (e.g., an internet connection) for communicating with a patient management server 196 that allows clinical personnel at remote locations to receive data from the remote monitoring device as well as issue commands. The controller may be programmed such when particular conditions are detected by the monitoring circuitry (such as when a measured parameter exceeds or falls below a specified limit value), the device transmits an alarm message to the remote monitoring device and to the patient management server to alert clinical personnel.

Figure 3:
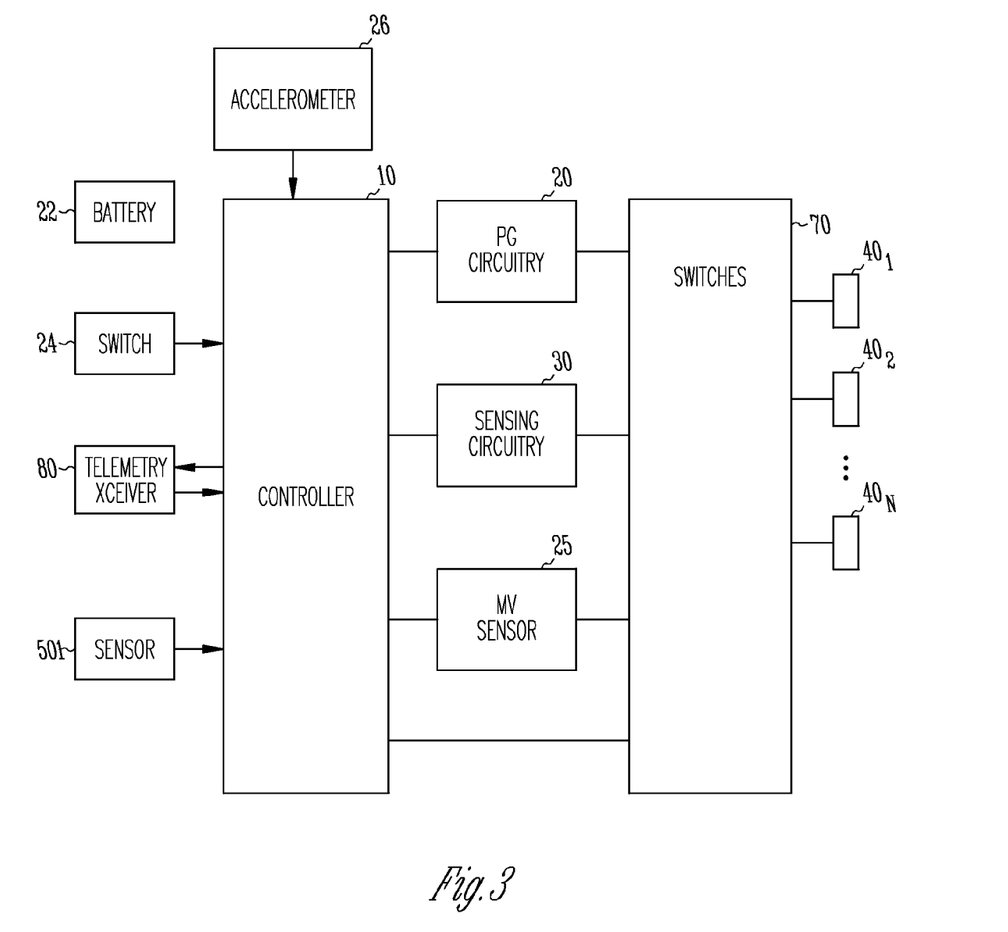
FIG. 3 is a block diagram of the electronic circuitry of an exemplary device.

A block diagram of the circuitry 132 is illustrated in FIG. 3. A battery 22 supplies power to the circuitry. The controller 10 controls the overall operation of the device in accordance with programmed instructions and/or circuit configurations. The controller may be implemented as a microprocessor-based controller and include a microprocessor and memory for data and program storage, implemented with dedicated hardware components such as ASICs (e.g., finite state machines), or implemented as a combination thereof. The controller also includes timing circuitry such as external clocks for implementing timers used to measure lapsed intervals and schedule events. As the term is used herein, the programming of the controller refers to either code executed by a microprocessor or to specific configurations of hardware components for performing particular functions. A telemetry transceiver 80 is interfaced to the controller which enables the controller to communicate with an external programmer and/or a remote monitoring unit. A magnetically or tactilely actuated switch 24 is also shown as interfaced to the controller to allow the patient to signal certain conditions or events to the implantable device. Sensing circuitry 30 and pulse generation circuitry 20 are interfaced to the controller by which the controller interprets sensing signals and controls the delivery of pacing pulses in accordance with a pacing mode. The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The pulse generation circuitry 20 delivers pacing pulses to pacing electrodes disposed in the heart and includes capacitive discharge pulse generators, registers for controlling the pulse generators, and registers for adjusting pacing parameters such as pulse energy (e.g., pulse amplitude and width). The device allows adjustment of the pacing pulse energy in order to ensure capture of myocardial tissue (i.e., initiating of a propagating action potential) by a pacing pulse. The pulse generation circuitry may also include a shocking pulse generator for delivering a defibrillation/cardioversion shock via a shock electrode upon detection of a tachyarrhythmia.

A pacing channel is made up of a pulse generator connectable to an electrode, while a sensing channel is made up of a sense amplifier connectable to an electrode. (As the terms are usually used, a sensing channel or pacing channel may be taken to mean either the physical components that actually make up the channel while in use such as the pulse generation or sensing circuitry together with the electrodes connected thereto or may be taken to mean only the pulse generation circuitry or sensing circuitry together with appropriate output or input ports for connecting to electrodes. Unless indicated otherwise, the latter definition will be used herein.) Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or pacing channels. The switch matrix 70 allows selected ones of the available implanted electrodes to be connected to sensing and/or pacing channels in either unipolar or bipolar configurations. A bipolar sensing or pacing configuration refers to the sensing of a potential or output of a pacing pulse between two closely spaced electrodes, where the two electrodes are usually on the same lead (e.g., a ring and tip electrode of a bipolar lead or two selected electrodes of a multi-polar lead). A unipolar sensing or pacing configuration is where the potential sensed or the pacing pulse output by an electrode is referenced to the conductive device housing or another distant electrode.

The device illustrated in FIG. 3 may be configured with multiple sensing and/or pacing channels that may be either atrial or ventricular channels depending upon the location of the electrode. The device is therefore capable of delivering single-site or multiple site ventricular pre-excitation pacing for purposes of stress reduction/augmentation as well as conventional pacing. The switch matrix allows particular myocardial sites to be pre-excited for purposes of stress reduction or augmentation by selecting the appropriately disposed electrode(s) to be incorporated into a pacing channel used to deliver pre-excitation pacing. Configuration of pacing and sensing channels may be performed via an external programmer communicating through the telemetry interface as well as automatically by the device when switching to or from different pacing modes.

Pre-excitation pacing may be delivered as single-site pacing, biventricular pacing where one of the ventricles is pre-excited relative to the other as determined by a programmed biventricular offset interval, or delivered as multi-site ventricular pacing. In the case where the pre-excitation pacing is delivered at multiple sites, the sites may be paced simultaneously or in accordance with a particular pulse output sequence that specifies the order and timing in which the sites are to be paced during a single beat. When an electrogram signal in an atrial or ventricular sensing channel exceeds a specified threshold, the controller detects an atrial or ventricular sense, respectively, which pacing algorithms may employ to trigger or inhibit pacing. The controller is capable of operating the device in a number of programmed modes where a programmed mode defines how pacing pulses are output in response to sensed events and expiration of time intervals. Pre-excitation pacing of one or more ventricular sites in proximity to, or remote from, a vulnerable region may be delivered in conjunction with a bradycardia pacing mode, which refers to a pacing algorithm that enforces a certain minimum heart rate, and may include or not include pacing pulses delivered to the atria or ventricles for other purposes (e.g., treatment of bradycardia). Inhibited demand bradycardia pacing modes utilize escape intervals to control pacing in accordance with sensed intrinsic activity. In an inhibited demand ventricular pacing mode, the ventricle is paced during a cardiac cycle only after expiration of a defined escape interval during which no intrinsic beat by the chamber is detected. For example, a ventricular escape interval can be defined between ventricular events so as to be restarted with each ventricular sense or pace, referred to as a lower rate interval (LRI). The inverse of this escape interval is the minimum rate at which the pacemaker will allow the ventricles to beat, sometimes referred to as the lower rate limit (LRL). Paces may also be delivered in a rate-adaptive pacing mode where the escape intervals are modified in accordance with a measured exertion level such as with accelerometer 26 or minute ventilation sensor 25. In atrial tracking and AV sequential pacing modes, another ventricular escape interval is defined between atrial and ventricular events, referred to as the atrio-ventricular delay or AVD interval. The atrio-ventricular delay interval is triggered by an atrial sense or pace and stopped by a ventricular sense or pace. A ventricular pace is delivered upon expiration of the atrio-ventricular delay interval if no ventricular sense occurs before the expiration.

In one embodiment, a cardiac rhythm management device includes at least one pacing channel for delivering pacing pulses to a selected ventricular myocardial site and a controller for controlling the delivery of pacing pulses in accordance with a programmed pacing mode. The controller is programmed to intermittently switch from a normal operating mode to an IPT mode in which a particular region or regions of the ventricular myocardium are subjected to increased or decreased mechanical stress as compared with the stress experienced by those regions during the normal operating mode. The normal operating mode may be a mode in which no pacing therapy is delivered or may be a primary pacing mode for delivering ventricular and/or atrial pacing therapy where the IPT pacing mode causes a different depolarization pattern than the primary pacing mode by, for example, exciting the ventricular myocardium at a site or sites different from the primary pacing mode or with different timing relationships between senses or paces. The switch from a primary pacing mode to an IPT mode may involve switching from bipolar pacing to unipolar pacing or vice-versa, switching which electrode of a bipolar pacing lead is the cathode and which electrode is the anode, switching from left ventricle-only pacing to right ventricular pacing or vice-versa, switching from biventricular pacing to single ventricular pacing or vice-versa, using at least one pacing channel in the stress augmentation mode that not used in the primary pacing mode, switching between different bradycardia pacing modes (e.g., between VVI and an atrial tracking or AV sequential mode), or modifying one or more escape intervals such as the AVD or LRL (e.g., the IPT mode may involve higher rate pacing, overdrive pacing, or may involve pacing with a shortened AVD such as an AVD specified as a percentage of the patient's intrinsic atrio-ventricular interval). The controller may be programmed to deliver IPT intermittently according to specified duty cycles as scheduled by an internal timer. For example, the scheduled duty cycles may specify that IPT is to be turned on for five minutes and turned off for five minute in a repetitive manner over a predetermined time period.

Titration of Intermittent Pacing Therapy

Ventricular dyssynchrony is the desired result of pre-excitation pacing to redistribute myocardial stress for a cardioprotective effect. Such dyssynchrony is what is responsible for causing the difference in stress experienced by the pre-excited and later-excited regions. As discussed above, intermittent periods of cardiac stress brought about by pacing therapy that produces relatively asynchronous cardiac contractions can exert a cardioprotective effect that reverses deleterious cardiac remodeling and/or provides protection against subsequent ischemic episodes. Described herein is a method and device for delivering intermittent pacing therapy (IPT) in a titrated manner dependent upon a patient's measured exertion level and/or sensed or paced heart rate (the paced heart rate may be a sensor-indicated rate as determined by an exertion level sensor in a rate-adaptive pacing mode). For example, if the patient has a high heart rate (either intrinsic or paced) or is active at the time of therapy, pacing parameters which produce smaller stress are used for the IPT mode. Otherwise, during periods of relative inactivity or low heart rate, parameters that generate larger stress are used for the IPT mode. Examples of pacing parameters that may be adjusted for this purpose are therapy duration, pacing rate, and AV delay. The pacing parameters and the patient status (heart rate, exercise status) can be trended and made available on a programmer or other external device for review.

Figure 4:
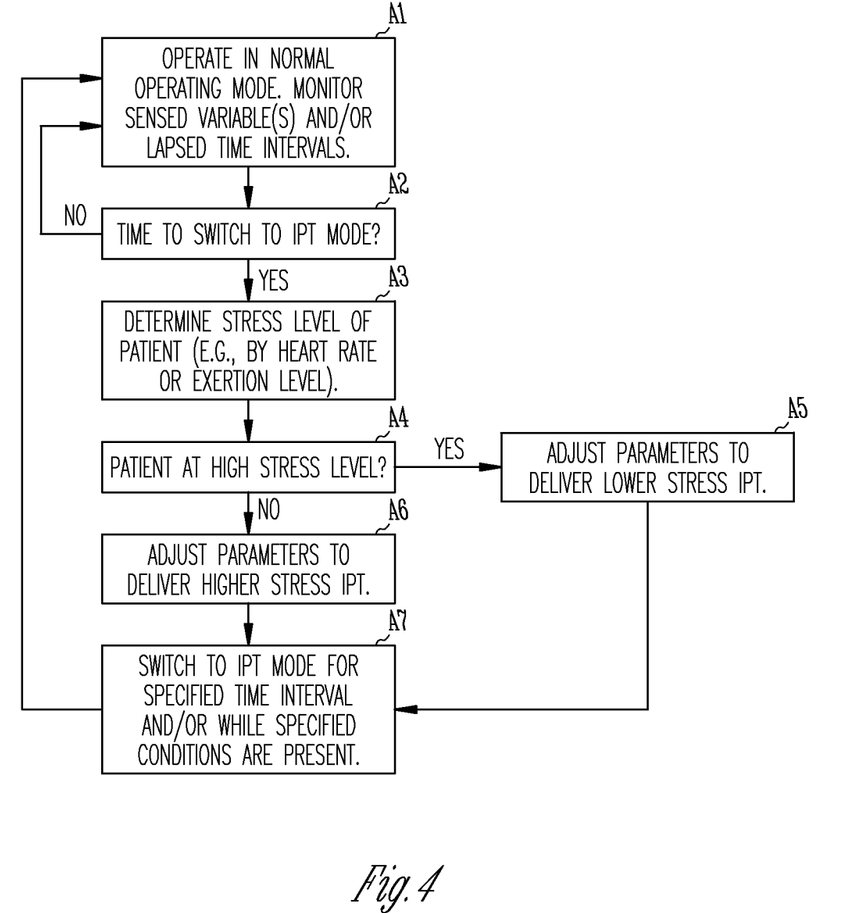
FIG. 4 illustrates an exemplary algorithm for titrating IPT.

FIG. 4 illustrates an algorithm that could be executed by the device controller in order to titrate the delivery of IPT therapy. At state A1, the device operates in a normal operating mode while monitoring lapsed time intervals and/or one or more sensed variables and checks at state A2 if it is time to switch to the IPT mode. The scheduling of the IPT mode may be based upon timed intervals and/or upon one or more sensed conditions being present (e.g., when the patient's heart rate and/or measured exertion level is within a particular range. The duration of the IPT mode may also be based upon lapsed time intervals and/or sensed conditions. When it is determined that a switch to the IPT mode is to be made, the device next determines the patient's present stress level at state A3. The determination of the stress level may be based upon any sensed variable(s) that is correlated in some manner with stress such as heart rate, exertion level (e.g., by a minute ventilation sensor or accelerometer), or heart rate variability. If it is determined that the patient is at a high stress level at state A4, one or more IPT parameters are adjusted to deliver lower stress IPT at state A5. Otherwise, one or more IPT parameters are adjusted at state A6 to deliver higher stress IPT. The device then switches to the IPT mode at state A7 for the prescribed period.

As described above, one way of implementing the scheduling of IPT is with timed duty cycles, such as with an on and off duration of five minutes each. The timing of such duty cycles may be adjusted based on the patient's heart rate and/or exercise status such that the higher the heart rate or activity level, the shorter the duration of the IPT duty cycle. Longer IPT duty cycles are used at low heart rates in order to increase the stress produced when the patient is relatively inactive. The functional relationship between the IPT duty cycle durations and the measured heart rate may be defined as a correspondence between different values of the variables (e.g., as implemented by a look-up table) or as an explicit calculation (The same may be said for all of the functional relationships described herein.) For example, the functional relationship between IPT duration and heart rate may be linear, sigmoidal, continuous or discrete, or expressed as a polynomial. For example, IPT may be delivered at a duty cycle of 30 secs ON and OFF when the heart rate is at a normal rate of 80 bpm. The duty cycle is then adjusted such that:

At heart rate of 100 bpm: 80/100*30=24 secs ON and OFF
At heart rate of 60 bpm: 80/60*30=40 secs ON and OFF In another embodiment, rather than adjusting the duty cycles of IPT in accordance with heart rate, the durations of IPT duty cycles are made dependent upon counted heart beats. For example, the device may operate with therapy ON (IPT mode) for M beats and with therapy OFF (normal mode) for N beats, where M and N are programmable integer values. The beats can be all cardiac cycles (including intrinsic and paced) or paced-only cardiac cycles. If paced cardiac cycles are used, then an upper limit on the total number of cardiac cycles for the therapy ON and OFF mode may be enforced. For example, the device may operate such that the total number of cardiac cycles can not exceed 1.5 times the specified number M paced beats in the ON mode and 1.5 times the specified number N paced beats in the OFF mode. These limits may be selected by the user.

Another way of implementing IPT is with a fixed overdrive pacing rate, e.g., 10 bpm above the patient's intrinsic heart rate delivered in accordance with timed or otherwise predetermined duty cycles. In one embodiment, the delivery of such IPT is titrated in accordance with the patient's intrinsic heart rate. For example, the IPT pacing rate may be specified to be 10% above the patient's intrinsic heart rate such that the IPT rate will be 110 bpm for an intrinsic rate of 100 bpm and 66 bpm for an intrinsic rate of 60 bpm. In another embodiment, the amount of overdrive pacing varies with heart rate in an inverse fashion such that the lower the heart rate, the more aggressive the IPT therapy. For example, the titration scheme may specify a maximum 20% rate increase at 60 bpm and minimum 5% rate increase at 100 bpm such that when the heart rate 80 bpm, the rate increase is:

$$5\%+(80-60)/(100-60)*(20\%-5\%)=12.5\%(16\ bpm)$$

In another embodiment, the IPT overdrive pacing rate is adjusted based on the patient's activity status as measured by an exertion level sensor such that when IPT delivered during exercise, the IPT overdrive pacing rate is reduced and when IPT is delivered at rest, the IPT overdrive pacing rate is increased. In an exemplary implementation, an activity coefficient for overdrive rate adjustment is multiplied with the specified IPT pacing rate such that if the patient is at rest, the coefficient is set at 1, while if the patient is exercising, the coefficient is set at a value less than 1 (e.g., 0.5 so that the overdrive pacing will be reduced by half. The coefficient may be made to vary with the exercise intensity in accordance with any functional relationship such that the more intense the exercise, the smaller the coefficient.

In another embodiment, the IPT mode involves delivering paces in an AV sequential or atrial tracking mode with a specified AVD interval. The value of the AVD used in the IPT mode is then adjusted based upon on heart rate and/or exercise status such that at a higher heart rate or during exercise, a small or medium stress amount is produced by the IPT. At a lower heart rate and when the patient is at rest, on the other hand, the AVD is adjusted to produce a larger amount of stress. In one embodiment, appropriate for patients who exhibit a relatively wide QRS interval (e.g., QRS>150 ms), is to adjust the AVD as follows in order to produce the desired amount of stress:

Small Stress: Short AVD (loose atrial kick)
Medium Stress: Long AVD (dyssynchronous contraction, MR)
Large Stress: Short/Long AVD with VV delay (e.g., where the RV is paced before the LV)

In patients who exhibit a relatively narrow QRS interval (e.g., 120<QRS<150 ms), on the other hand, the AVD interval may be adjusted to produce the desired amount of stress as follows:

Small Stress: Medium AVD (approx. 50% of intrinsic AV interval)
Medium Stress: Short AVD (dyssynchronous contraction)
Large Stress: Short AVD with VV delay (e.g., where the RV is paced before the LV)

EXEMPLARY EMBODIMENTS

As described herein, a cardiac device for delivering intermittent pacing therapy (IPT) may include one or more sensing channels for sensing electrical cardiac activity, one or more pacing channels for delivering pacing pulses to one or more myocardial sites, a controller programmed to operate the device in either a normal operating mode or an IPT mode where, in the IPT mode, the controller is programmed to deliver paces to the one or more myocardial sites using a pacing mode that results in some degree of ventricular dyssynchrony as compared with the normal operating mode.

In one embodiment, the controller is programmed to: 1) switch to the IPT mode according to a timed duty cycle schedule in which the device operates in the IPT mode for A seconds and operates in the normal mode for B seconds; and, 2) modify the durations of the timed duty cycle such that the time duration values A and B are functions of a sensed or paced heart rate, where the paced heart rate may be a sensor-indicated rate. The controller may be programmed such that the duration of the IPT mode A increases if the heart rate decreases to a predetermined extent in accordance with a predetermined functional relationship.

In another embodiment, the controller is programmed to switch to the IPT mode according to a predetermined duty cycle schedule in which the device operates in the IPT mode for A heart beats and operates in the normal mode for B heart beats. The beat durations A and B may be programmable integer values or may be functions of a sensed or paced heart rate. The beat durations may refer to all cardiac cycles (including intrinsic and paced) or to paced-only cardiac cycles. If paced-only cardiac cycles are used to define the beat durations A and B, then an additional limit on the total number of cardiac cycles in either or both of the IPT and normal modes may be imposed. Such limits may be expressed as a function of the beat durations such as a proportionality factor programmable by the user. For example, the total beat duration of the IPT or normal mode may be constrained to be no more than 1.5 times the specified paced beat duration of that mode. In another embodiment, one of the durations A or B may be a beat duration while the other is a time duration. That is, the duration A of the IPT mode may be either a number of heart beats or an amount of time, and the duration B of the normal mode may be either a number of heart beats or an amount of time (where the beat and time durations may be either fixed programmable values or functions of heart rate).

In another embodiment, the controller is programmed to intermittently switch to the IPT mode according to a predetermined duty cycle where, in the IPT mode, the controller delivers paces in an overdrive mode at a pacing rate that is a percentage P above a sensed intrinsic heart rate. The controller may be programmed such that the value of the percentage P is a function of the sensed intrinsic heart rate. For example, the value of P may be made to vary inversely with the sensed intrinsic heart rate. The device may further include an exertion level sensor for measuring a patient's exertion level where the controller is programmed such that the value of the percentage P is a function of the measured exertion level. For example, the value of P may vary inversely with the measured exertion level.

In another embodiment, the controller is programmed to intermittently switch to the IPT mode according to a predetermined duty cycle and to deliver paces in the IPT mode in an AV sequential or atrial tracking ventricular pacing mode with a specified atrio-ventricular delay AVD. In the IPT mode, the controller delivers paces with an AVD that is a percentage P of a sensed intrinsic atrio-ventricular interval and is programmed to adjust the value of P in accordance with a sensed or measured heart rate and/or measured exertion level. In one implementation the controller is programmed to adjust the value of P such that P is decreased if the sensed or measured heart rate and/or measured exertion level increases to a predetermined extent in accordance with a predetermined functional relationship. In another implementation, the controller is programmed to adjust the value of P such that P is increased if the sensed or measured heart rate and/or measured exertion level increases to a predetermined extent in accordance with a predetermined functional relationship. The controller may also be programmed to deliver biventricular pacing in the IPT mode with an increased VV delay between the paces delivered to each of the ventricles if the sensed or measured heart rate and/or measured exertion level decreases to a predetermined extent in accordance with a predetermined functional relationship.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A cardiac device, comprising:
    one or more sensing amplifiers for forming sensing channels for sensing electrical cardiac activity;
    one or more pulse generators for forming pacing channels for delivering pacing pulses to one or more myocardial sites;
    a controller programmed to operate the device in either a normal operating mode or an intermittent pacing therapy (IPT) mode;
    wherein, in the IPT mode, the controller is programmed to deliver paces to the one or more myocardial sites using a pacing mode that results in some degree of ventricular dyssynchrony as compared with the normal operating mode;
    wherein the controller is programmed to:
    switch to the IPT mode according to a timed duty cycle schedule in which the device operates in the IPT mode for A seconds and operates in the normal mode for B seconds;
    set the IPT duty cycle duration values A and B as functions of a sensed or paced heart rate in which different heart rate values correspond to different duty cycle duration values and such that the IPT duty cycle duration value A is decreased in response to an increase in heart rate; and,
    deliver paces during the IPT mode at a pacing rate that is a specified percentage above the sensed heart rate wherein the specified percentage varies inversely with sensed heart rate.

2. The device of claim 1 wherein the controller is programmed such that the duration A of the IPT mode increases if the sensed or paced heart rate decreases to a predetermined extent in accordance with a predetermined functional relationship.

3. The device of claim 1 further comprising an exertion level sensor for modifying a pacing rate of the device.

4. The device of claim 1 wherein the normal operating mode is a mode in which no pacing therapy is delivered.

5. The device of claim 1 wherein the normal operating mode is a primary pacing mode for delivering ventricular and/or atrial pacing therapy where the IPT pacing mode causes a different depolarization pattern than the primary pacing mode.

6. The device of claim 5 wherein the controller is configured such that the IPT pacing mode excites myocardial sites different from the primary pacing mode.

7. The device of claim 5 wherein the controller is configured such that the IPT pacing mode excites the one or more myocardial sites with different timing relationships between senses or paces than the primary pacing mode.

8. The device of claim 5 wherein the controller is configured such that the switch from the primary pacing mode to the IPT mode involves switching from bipolar pacing to unipolar pacing.

9. The device of claim 5 wherein the controller is configured such that the switch from the primary pacing mode to the IPT mode involves switching from unipolar pacing to bipolar pacing.

10. The device of claim 5 further comprising a bipolar lead and wherein the controller is configured such that the switch from the primary pacing mode to the IPT mode involves switching the polarity of the bipolar pacing lead.

11. A method for operating a cardiac device, comprising:
sensing electrical cardiac activity;
delivering pacing pulses to one or more myocardial sites;
operating the device in either a normal operating mode or an intermittent pacing therapy (IPT) mode;
in the IPT mode, delivering paces to the one or more myocardial sites using a pacing mode that results in some degree of ventricular dyssynchrony as compared with the normal operating mode;
switching to the IPT mode according to a timed duty cycle schedule in which the device operates in the IPT mode for A seconds and operates in the normal mode for B seconds;
setting the IPT duty cycle duration values A and B as functions of a sensed or paced heart rate in which different heart rate values correspond to different duty cycle duration values and such that the IPT duty cycle duration value A is decreased in response to an increase in heart rate; and,
delivering paces during the IPT mode at a pacing rate that is a specified percentage above the sensed heart rate wherein the specified percentage varies inversely with sensed heart rate.

12. The method of claim 11 wherein the duration A of the IPT mode increases if the sensed or paced heart rate decreases to a predetermined extent in accordance with a predetermined functional relationship.

13. The method of claim 11 further comprising modifying a pacing rate of the device in accordance with a measured exertion level.

14. The method of claim 11 wherein the normal operating mode is a mode in which no pacing therapy is delivered.

15. The method of claim 11 wherein the normal operating mode is a primary pacing mode for delivering ventricular and/or atrial pacing therapy where the IPT pacing mode causes a different depolarization pattern than the primary pacing mode.

16. The method of claim 15 wherein the IPT pacing mode excites myocardial sites different from the primary pacing mode.

17. The method of claim 15 wherein the IPT pacing mode excites the one or more myocardial sites with different timing relationships between senses or paces than the primary pacing mode.

18. The method of claim 15 wherein the switch from the primary pacing mode to the IPT mode involves switching from bipolar pacing to unipolar pacing.

19. The method of claim 15 wherein the switch from the primary pacing mode to the IPT mode involves switching from unipolar pacing to bipolar pacing.

20. The method of claim 15 wherein the switch from the primary pacing mode to the IPT mode involves switching the polarity of a bipolar pacing lead.

* * * * *